(12) United States Patent
Grass et al.

(10) Patent No.: US 7,209,580 B2
(45) Date of Patent: Apr. 24, 2007

(54) FAST COMPUTED TOMOGRAPHY METHOD (75) Inventors: Michael Grass, Hamburg (DE);
Thomas Koehler, Norderstedt (DE);
Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 687 days.

(21) Appl. No.: 10/276,020

(22) PCT Filed: Mar. 8, 2002

(86) PCT No.: PCT/IB02/00697

§ 371 (c)(1),
(2), (4) Date: Nov. 12, 2002

(87) PCT Pub. No.: WO02/073174

PCT Pub. Date: Sep. 19, 2002

(65) Prior Publication Data

US 2003/0128869 A1 Jul. 10, 2003

(30) Foreign Application Priority Data

Mar. 12, 2001 (EP) ................................ 01200907

(51) Int. Cl.
G06K 9/00 (2006.01)
G06K 9/40 (2006.01)
A61B 6/00 (2006.01)
G01N 23/00 (2006.01)
G21K 1/12 (2006.01)
H05G 1/60 (2006.01)

(52) U.S. Cl. ..................... 382/131; 382/260; 378/14; 378/15

(58) Field of Classification Search ................ 382/128, 382/131, 132, 260; 378/4, 11, 14, 15
See application file for complete search history.

(56) References Cited

U.S. PATENT DOCUMENTS

| 4,149,248 | A | * | 4/1979 | Pavkovich | 378/14 |
|---|---|---|---|---|---|
| 4,333,145 | A | * | 6/1982 | Heuscher et al. | 600/425 |
| 4,593,355 | A | * | 6/1986 | Chase | 382/131 |
| 5,315,665 | A | | 5/1994 | Ohhashi | |
| 5,390,226 | A | * | 2/1995 | Tam | 378/19 |
| 5,463,666 | A | | 10/1995 | Eberhard et al. | |
| 5,878,103 | A | * | 3/1999 | Sauer et al. | 378/15 |
| 5,881,123 | A | | 3/1999 | Tam | |

(Continued)

FOREIGN PATENT DOCUMENTS

EP   0 990 892 A2   4/2000

*Primary Examiner*—Andrew W. Johns
*Assistant Examiner*—Anthony Mackowey (57) ABSTRACT The invention relates to a computed tomography method for forming images of an object to be examined which is arranged in an examination zone. The examination zone is scanned by means of a conical X-ray beam. In order to enable images having a high image quality to be formed from a selected imaging zone while making an as small as possible computational effort, the invention proposes the following steps:
a) selecting an imaging zone of the object to be examined,
b) determining the sub-regions of the X-ray detector on which the imaging zone of the object to be examined is projected during the acquisition of the projection data,
c) forming sub-projection data by selecting the projection data associated with the sub-regions from the acquired projection data, and
d) reconstructing the desired image from the sub-projection data by backprojection.

18 Claims, 4 Drawing Sheets

U.S. PATENT DOCUMENTS

| | | | |
|---|---|---|---|
| 5,900,878 A * | 5/1999 | Goto et al. | 345/419 |
| 6,078,639 A * | 6/2000 | Heuscher | 378/15 |
| 6,256,366 B1 | 7/2001 | Lai | |
| 6,292,527 B1 | 9/2001 | Guendel | |
| 6,327,326 B1 | 12/2001 | Flohr et al. | |
| 6,332,035 B1 | 12/2001 | Basu et al. | |
| 6,408,088 B1 * | 6/2002 | Hu | 382/131 |
| 6,829,379 B1 * | 12/2004 | Knoplioch et al. | 382/131 |

* cited by examiner

FAST COMPUTED TOMOGRAPHY METHOD

BACKGROUND

The invention relates to a computed tomography method for forming images of an object to be examined which is arranged in an examination zone, which method includes the steps of:
- generating, while using an X-ray source, a conical X-ray beam which traverses the examination zone or the object to be examined which is arranged therein,
- rotating the X-ray source and an oppositely situated X-ray detector on the other side of the examination zone along a trajectory around the examination zone,
- acquiring projection data by means of the X-ray detector during the rotation,
- reconstructing one or more images from the projection data.

The invention also relates to a corresponding computed tomography apparatus, notably an apparatus for carrying out such a computed tomography method.

A method of this kind is known from EP 0 990 892 A2. In order to reduce the computational effort required for the reconstruction of the absorption distribution in the examination zone, the cited document proposes to perform rebinning of measuring data so as to form a number of groups, to subject said data to one-dimensional filtering, and to reconstruct the spatial distribution of the absorption from the filtered data of different groups.

Future cone beam computed tomography systems will enable the formation of high-resolution 3D images from the acquired projection data. Moreover, the physician will additionally be offered novel possibilities for viewing. It will inter alia be possible to select a plane of arbitrary orientation in the examination zone wherefrom data was acquired and to form a slice image which is situated in said plane from the data available. Such a slice image in the desired plane is formed by interpolation of the 3D image data which constitutes a complete 3D image data set resulting from the reconstruction of the acquired projection data. Such an interpolation of 3D image data, however, gives rise to a pronounced deterioration of the image quality of such a slice image.

SUMMARY

Therefore, it is an object of the invention to devise the above computed tomography method and the corresponding computed tomography device in such a manner that images of a desired imaging zone can be formed with an as high as possible image quality while the required computational effort remains as small as possible nevertheless.

This object is achieved in accordance with the invention by means of computed tomography method which includes the following steps:
a) selecting an imaging zone of the object to be examined,
b) determining the sub-regions of the X-ray detector on which the imaging zone of the object to be examined is projected during the acquisition of the projection data,
c) forming sub-projection data by selecting the projection data associated with the sub-regions from the acquired projection data, and
d) reconstructing the desired image from the sub-projection data by backprojection.

The invention is based on the recognition of the fact that instead of deriving images of the desired imaging zone from already reconstructed 3D image data by interpolation, the projection data at the voxel positions (volume elements) within the desired imaging zone can be used directly for the reconstruction of the desired image of the imaging zone. However, in order to minimize the computational effort required for this purpose, the invention also poses the idea to use for the reconstruction, instead of all projection data acquired, only the projection data that is actually required for the reconstruction of the image of the desired imaging zone.

Thus, in accordance with the invention the overall quantity of projection data is reduced to sub-projection data wherefrom the desired image is reconstructed. Notably the backprojection is performed only on the basis of said sub-projection data. In order to reduce the projection data, it is then determined on which sub-regions of the X-ray detector the imaging zone is projected in the individual imaging positions. Only the projection data that is acquired in these detector regions will form the sub-projection data.

Thus, the invention offers an improved image quality for images of individual imaging zones as well as minimizes the computational effort required, so that the reconstruction of such images may be very fast. The method in accordance with the invention can be used not only for forming slice images of arbitrary orientation in the object to be examined, but is in principle also suitable for the formation of arbitrary images from the examination zone, for example, for the formation of images of individual sub-volumes, individual lines, planes or arbitrary surfaces, for example, curved surfaces of objects which are situated in the examination zone, for example, specific organs.

In conformity with a method of the invention it is proposed to perform first some pre-processing steps of the reconstruction on the basis of the complete projection data and to perform subsequently the reduction of the projection data to sub-projection data. In conformity with an alternative version, however, the reduction to the sub-projection data takes place already after the acquisition of the projection data, so that the pre-processing steps of the reconstruction method already are performed exclusively while using the sub-projection data. The choice of the relevant version of the method is dependent essentially on which reconstruction method per se is to be used for the formation of images. However, the type of desired images or the selection of the imaging zone may also play a part in the choice of the relevant version of the method.

Figure 2:
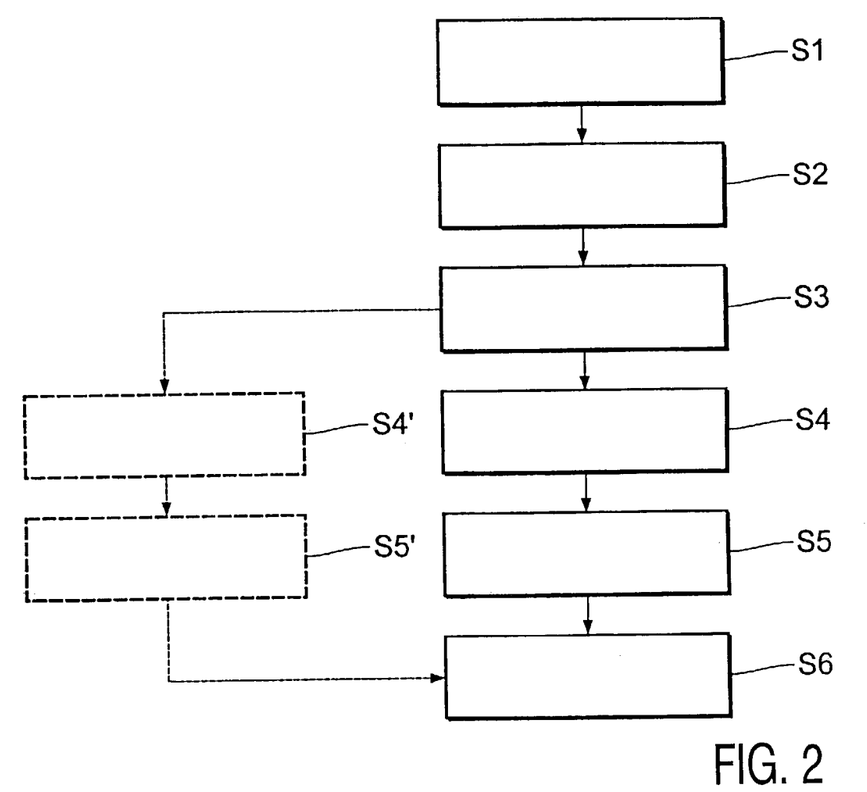
FIG. 2 shows a flow chart illustrating the execution of the computed tomography method in accordance with the invention.

According to the method which is known from the cited EP 0 990 892 A2, whose description is hereby incorporated herein by way of reference, for example, the steps 101 to 108 of the method as shown in FIG. 2 may be considered to be pre-processing steps of the reconstruction method, said steps being applied to the complete projection data, after which in accordance with the invention the reduction to the (already pre-processed) sub-projection data takes place, the latter data being used exclusively for the backprojection.

For the special case where the region of the X-ray detector on which the imaging zone is projected is very small, it may be effective to replace the filtering steps that are necessary in the context of the pre-processing for the reconstruction by convolutions in the spatial domain. For such convolution it is merely necessary to enlarge the region on which the projection data is projected in the spatial domain. Overall, however, a saving in respect of computational effort and hence computing time can thus be achieved in given circumstances.

The further version of the method in accordance with the invention enables an as large as possible saving of computational effort to be achieved. The projection data set obtained for each X-ray source position during the acquisition of the projection data is then analyzed as to which projection data are required for the formation of an image of the desired imaging zone, and each individual projection data set is then reduced to a sub-projection data set. When, for example, 100 projection data sets are formed during the acquisition of the projection data in 100 different X-ray source positions, these sets are individually analyzed according to this version and therefrom 100 different sub-projection data sets are determined so as to be further processed in forming the desired images in accordance with the invention.

In conformity with another aspect of the invention the acquisition of the projection data preferably takes place along a circular or helical trajectory around the object to be examined. However, other trajectories such as, for example, two semi-circles or two full circles which are tilted relative to one another can also be used, and also preferably symmetrical trajectories.

The object in accordance with the invention is also achieved by means of a computed tomography device which may be elaborated further in the same or identical way as the described method.

In accordance with one aspect of the invention, a computed tomography method for forming images of an object to be examined which is arranged in an examination zone is provided. The method includes the steps of generating, while using an X-ray source, a conical X-ray beam which traverses the examination zone or the object to be examined which is arranged therein; rotating the X-ray source and an oppositely arranged X-ray detector on the other side of the examination zone along a trajectory around the examination zone; acquiring projection data by means of the X-ray detector during the rotation; reconstructing one or more images from the projection data; selecting an imaging zone of the object to be examined; determining the sub-regions of the X-ray detector on which the imaging zone of the object to be examined is projected during the acquisition of the projection data; forming sub-projection data by selecting the projection data associated with the sub-regions from the acquired projection data; and reconstructing the desired image from the sub-projection data by backprojection.

In accordance with a more limited aspect of the invention, the pre-processing steps for the reconstruction, notably weighting, logarithmation, filtering and/or rebinning of the projection data, are performed on the basis of the complete, acquired projection data and subsequently the sub-projection data are formed and the further reconstruction steps are executed.

In accordance with a more limited aspect of the invention, the sub-projection data are joined and subsequently the pre-processing steps for the reconstruction, notably weighting, logarithmation, filtering and/or rebinning of the projection data, as well as the further reconstruction steps are performed exclusively on the basis of the sub-projection data.

In accordance with a more limited aspect of the invention, the pre-processing step of filtering is replaced by local convolution for selected sub-projection data, that is, notably when the sub-region of the X-ray detector which is associated with the selected sub-projection data and on which the imaging zone of the object to be examined is projected is small.

In accordance with a more limited aspect of the invention, the projection data are acquired as respective single projection data sets for each X-ray source position, and a respective sub-projection data set is determined for each projection data set.

In accordance with a more limited aspect of the invention, for the acquisition of the projection data the X-ray source and the X-ray detector rotate along a circular or helical trajectory around the object to be examined.

In accordance with another aspect of the invention, A computed tomography device for forming images of an object to be examined which is arranged in an examination zone is provided. The device includes an X-ray source for generating a conical X-ray beam which traverses the examination zone or the object to be examined which is arranged therein; means for rotating the X-ray source and an oppositely situated X-ray detector on the other side of the examination zone along a trajectory around the examination zone; an X-ray detector for the acquisition of projection data during the rotation; means for reconstructing one or more images from the projection data; means for selecting an imaging zone of the object to be examined; means for determining the sub-regions of the X-ray detector on which the imaging zone of the object to be examined is projected during the acquisition of the projection data; means for forming sub-projection data by selecting the projection data associated with the sub-regions from the acquired projection data; and means for reconstructing the desired image from the sub-projection data by backprojection.

DRAWINGS

The invention will be described in detail hereinafter with reference to the drawing. Therein.

DESCRIPTION

Figure 1:
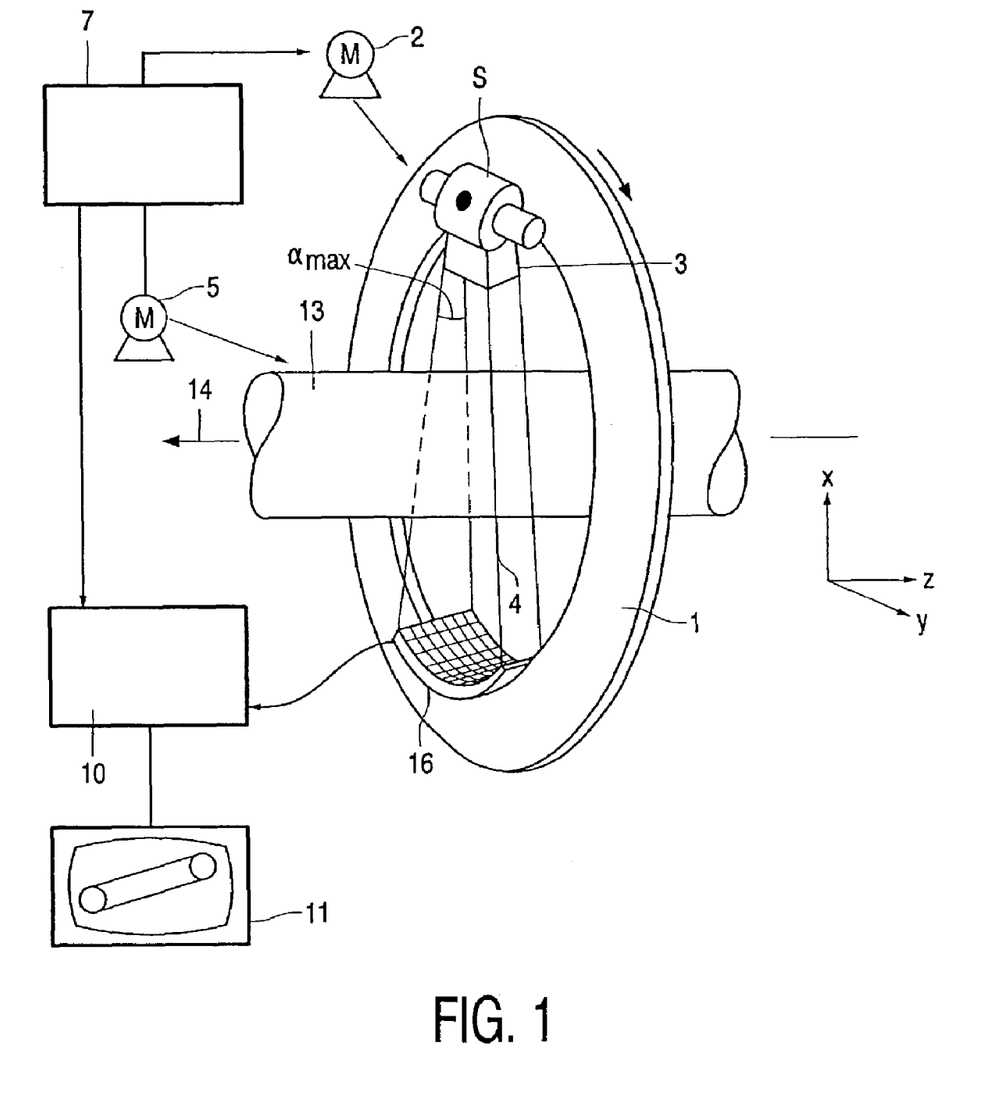
FIG. 1 shows a computed tomography device in accordance with the invention.

The computed tomography device as shown in FIG. 1 includes a gantry 1 which is capable of rotating around an axis of rotation 14 which extends parallel to the z direction. To this end, the gantry 1 is driven by a motor 2. The gantry 1 accommodates a radiation source S, for example, an X-ray source, which is provided with a collimator device 3 for forming a conical radiation beam 4. The radiation beam 4 penetrates an examination zone 13 in which an object to be examined, for example, a patient on a patient table (both of which are not shown), may be arranged. After having traversed the examination zone 13, the radiation beam 4 is incident on a two-dimensional detector unit 16 which is also mounted on the gantry 1 and includes a number of detector rows, each of which comprises a plurality of detector elements. In each radiation source position each detector element delivers a measuring value for a ray of the radiation beam 4. All measuring values for all radiation source positions together form the above-mentioned projection data.

The angle of aperture of the radiation beam 4, denoted by the reference $\alpha_{max}$, determines the diameter of the examination zone 13 within which the object to be examined is situated during the acquisition of the projection data. Furthermore, the object to be examined can also be displaced, by means of a motor 5, in the direction parallel to the axis of rotation, for example, in order to enable the acquisition of the projection data along a helical trajectory.

The projection data acquired by the detector unit 16 is applied to an image processing unit 10 which reconstructs therefrom the absorption distribution in a desired imaging zone of the examination zone 13, for example, for display on a monitor 11. The two motors 2, 5, the image processing unit 10, the radiation source S and the transfer of the acquired projection data from the detector unit 16 to the image processing unit 10 are controlled by a suitable control unit 7. For further details of the device shown in FIG. 1, reference is made again to the cited EP 0 990 892 A2.

FIG. 2 shows a flow chart containing the essential steps of the method in accordance with the invention. During a first step S1, projection data is acquired from the examination zone of an object to be examined, said data being stored. For the purpose of acquisition the X-ray source and the X-ray detector rotate along a predetermined trajectory, for example, along a helical trajectory T as shown by way of example in FIG. 3. A respective projection data set is acquired in a large number of discrete points along said trajectory T and all projection data sets together constitute said projection data.

Figure 3:
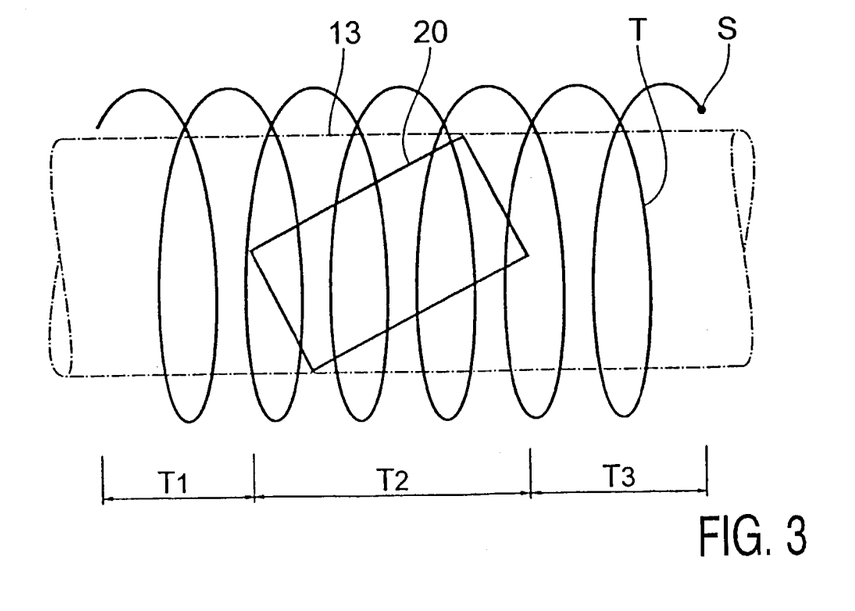
FIG. 3 shows a trajectory used in the context of the invention.

During the subsequent step S2 of the method the imaging zone for which an image is to be formed is chosen, for example, by an attending physician. As is shown in FIG. 3, such an image may be an image of an inclined slice 20 of the examination zone 13. However, for example, a curved surface of a given object within the examination zone 13, for example, the surface of an organ, a given sub-volume of the examination zone 13 or a line within this object may also be selected as the imaging zone.

Figure 4:
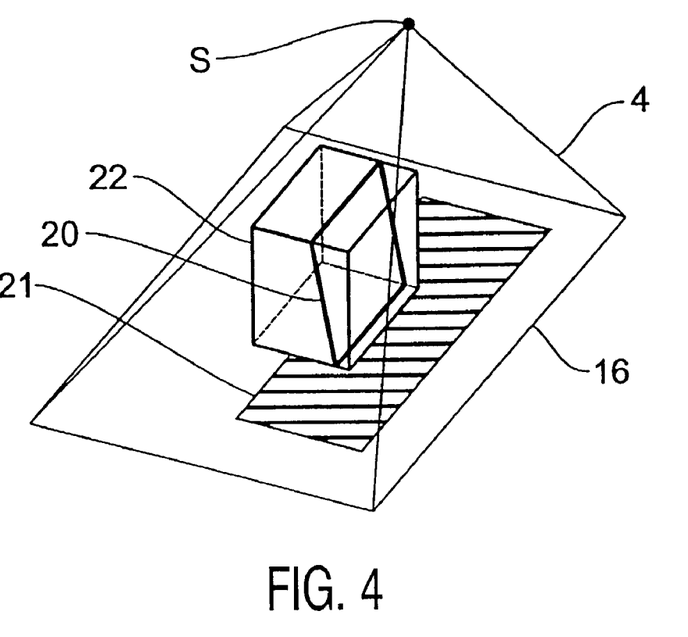
FIG. 4 illustrates an imaging zone given by way of example, FIG. 5 further illustrates the imaging zone.

During the third step S3 of the method it is determined onto which sub-regions the desired imaging zone, that is, the slice 20 in the example shown in FIG. 3, was projected in the individual imaging positions, that is, the positions along the trajectory T in which a respective projection data set was acquired. This is shown in detail for a single trajectory position in FIG. 4. It appears that within the reconstruction volume 22 that can be completely imaged the inclined plane 20 is imaged only on the region 21 of the detector 16. Thus, if only a slice image of the plane 20 is to be formed, only the projection data acquired in the region 21 of the detector 16 need be processed further whereas all further projection data acquired by the detector 16 in the imaging position shown need not be processed further for such an image. In accordance with the invention this examination is preferably performed for all trajectory positions because, as is clearly shown, in each trajectory position the inclined slice 20 is projected onto a different detector region which may also be larger or smaller than the detector region 21 shown in FIG. 4.

Moreover, there may also be imaging positions along the trajectory T in which a desired imaging zone is not at all projected onto the detector 16. This can be seen in FIG. 3. As can be readily observed, the slice 20 is not at all imaged on the detector in imaging positions along the sub-regions T1 and T3 of the trajectory T, but is imaged thereon in the sub-region T2. Projection data originating from the sub-regions T1 and T3, therefore, can also be excluded from further processing when only a slice image of the slice 20 is to be formed.

The sub-projection data are formed in the step S4 as previously mentioned. For the further processing only the projection data that also contain information on the imaging zone, as determined in the step S3, are then selected. Preferably, for each projection data set a sub-projection data set is then formed, the sum of the sub-projection data sets forming the totality of sub-projection data.

The desired image of the imaging zone is subsequently reconstructed in the steps S5 and S6, the pre-processing steps being combined in the step S5 of the method whereas the step S6 of the method comprises the actual backprojection from the sub-projection data. The step S5 of the method includes notably pre-processing steps, such as weighting of the sub-projection data, logarithmation, filtering and/or calibration. Rebinning may also form part of the pre-processing steps. The pre-processing steps specifically used are dependent essentially on the reconstruction method used. In the case of the reconstruction method which is known from EP 0 990 892 A2 or the known Feldkamp method with helical scanning, the steps 101 to 108 involved therein are among the pre-processing steps. Other reconstruction methods, for example, after scanning along a circular trajectory, however, do not include rebinning and also partly use convolution operations instead of filter operations.

As is already indicated in dashed lines in FIG. 2, the method may also be modified. For example, after the third step S3 of the method a pre-processing of the complete projection data (step S4') may take place and the sub-projection data may be formed subsequently (step S5') from the already pre-processed complete projection data. The backprojection of the last step of the method (S6), however, again involves only the sub-projection data according to this modification. A further modification may include that the pre-processing of the complete projection data takes place already after the acquisition of the projection data, meaning that the step S5 of the method takes place already after the first step S1 of the method, and that the selection of the desired imaging zone (S2) and the further steps S3, S4 and S6 of the method take place only after that.

Figure 5:
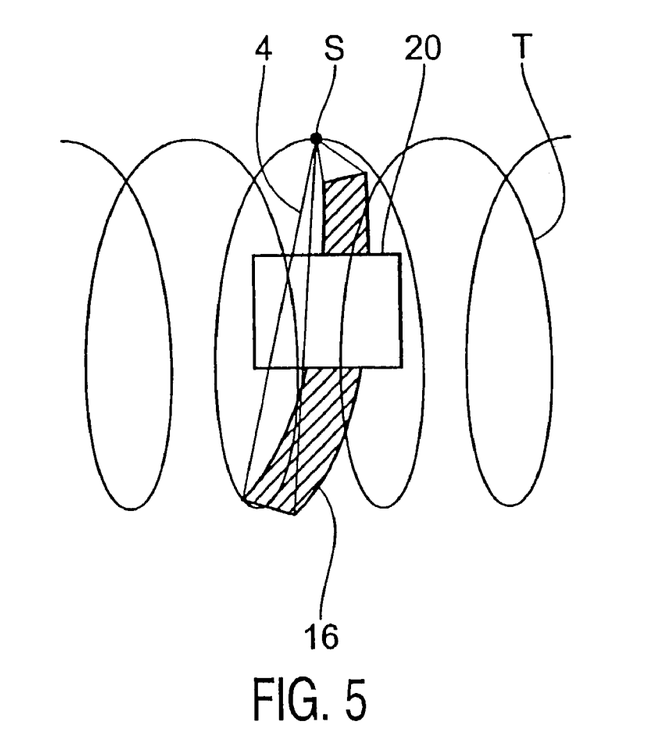
Figure 6:
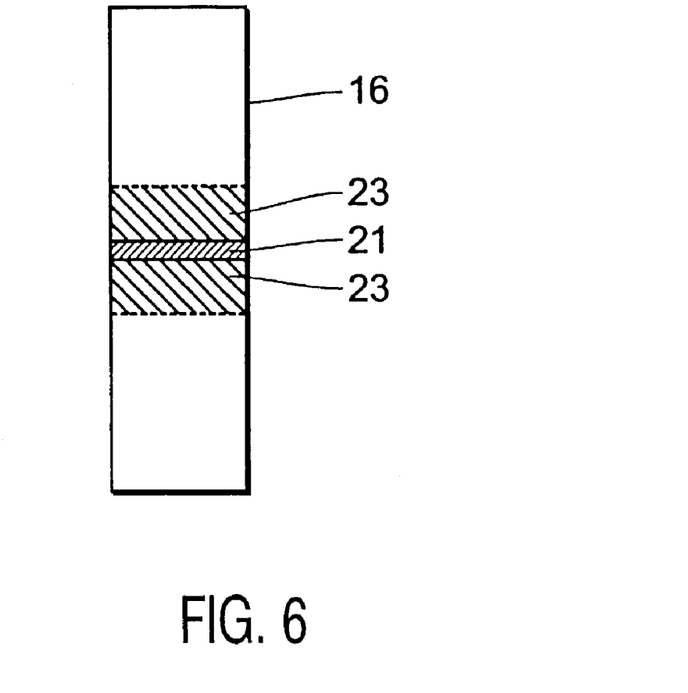
FIG. 6 shows the projection of such an imaging zone on an X-ray detector.

FIG. 5 again shows the trajectory T which is already shown in FIG. 3. Furthermore, the position of the X-ray source S, of the detector 16 and of the X-ray beam 4 is shown for a fixed trajectory position, and also their relative position with respect to the imaging zone, again being the inclined slice 20 in the present example. FIG. 6 is a more accurate illustration of the sub-region of the detector 16 on which the imaging zone 20 is projected in this trajectory position. The narrow sub-region 21 of the detector 16 represents the region on which the slice 20 is projected; this means that only projection data in the sub-region 21 contain information concerning the slice 20. Because this sub-region 21 is a very narrow and small sub-region of the overall detector surface 16, notably with a view to the necessary computing time it may be advantageous to perform the filtering step, necessary for the reconstruction, locally and not across the entire detector 16; this means that it may be advantageous to replace the filtering step in the time domain by a simple convolution in the spatial domain; which operation would generally be too intricate for the complete projection data from the overall detector region 16. In order to enable such convolution to be performed for the example shown, the sub-region 21 must be enlarged by way of corresponding side regions 23 on both sides. Convolution can then be performed in said enlarged region, said convolution possibly requiring less computational effort than a corresponding filter operation. The described modification can also be incorporated in the described method, notably in the necessary pre-processing steps.

Figure 7:
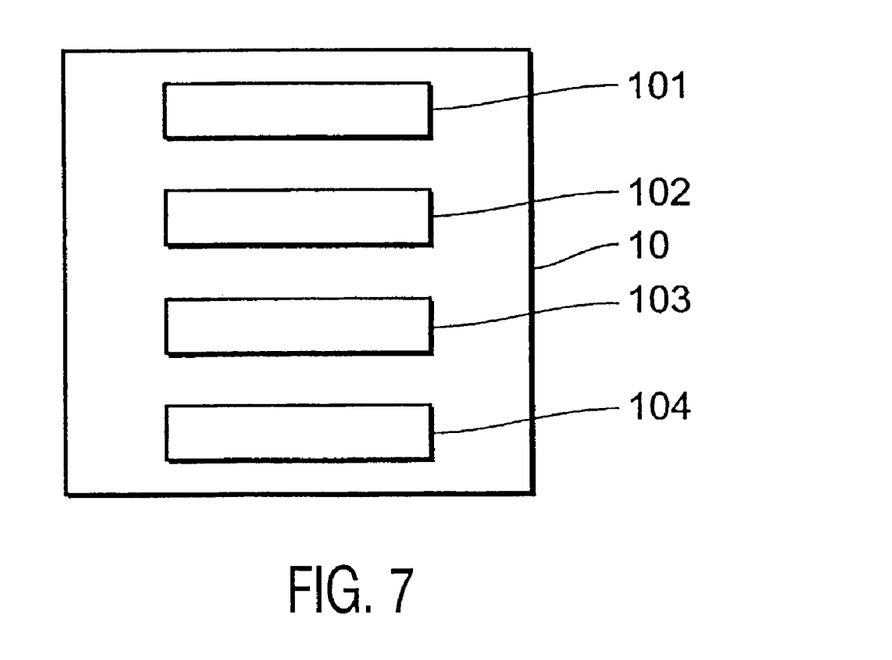
FIG. 7 shows the construction of an image processing unit in accordance with the invention.

FIG. 7 is a detailed representation of the processing unit 10 of the computed tomography device in accordance with the invention. The processing unit 10 in accordance with the invention includes means 101 for selecting an imaging zone of the object to be examined. These means may include, for example, in that the physician can mark the imaging zone to be reproduced in a separate image on the display screen by means of a pointer. Furthermore, the processing unit 10 includes means 102 which enable determination of the regions of the X-ray detector on which the imaging zone has been projected during the acquisition of the projection data. There are also provided means 103 for forming the sub-projection data as well as means 104 for reconstructing the desired image by backprojection from the sub-projection data. The means 102, 103 and 104 are preferably implemented as suitable arithmetic units.

The method in accordance with the invention enables the formation of images from selected imaging zones which have a significantly higher image quality than images derived from 3D volume data by interpolation. Moreover, the method in accordance with the invention is capable of reducing the required computation time in conformity with the respective dimensions and position of the desired imaging zone.

The invention has been described with reference to the preferred embodiment. Obviously, modifications and alterations will occur to others upon reading and understanding the preceding description. It is intended that the invention be construed as including all such modifications and alterations insofar as they come within the scope of the appended claims or the equivalents thereof.

The invention claimed is:

1. A computed tomography method for forming images of an object to be examined which is arranged in an examination zone, which method includes the steps of:
   generating, while using an X-ray source, a conical X-ray beam which traverses the examination zone of the object to be examined which is arranged therein;
   rotating the X-ray source and an oppositely arranged X-ray detector on the other side of the examination zone along a trajectory around the examination zone;
   acquiring projection data from the X-ray detector during the rotation;
   reconstructing one or more images from the projection data;
   using the one or more images to select an imaging zone of the object to be examined, wherein the selected imaging zone of the object has a spatial orientation different from a spatial orientation of the one or more reconstructed images;
   determining sub-regions of the X-ray detector on which the imaging zone of the object to be examined is projected during the acquisition of the projection data;
   forming sub-projection data by selecting the projection data associated with the sub-regions from the acquired projection data; and
   reconstructing one or more images of the selected imaging zone from the sub-projection data.

2. A computed tomography method as claimed in claim 1, further including the step of pre-processing the projection data, wherein the pre-processing step, notably weighting, logarithmation, filtering and/or rebinning of the projection data, is performed on the basis of the complete, acquired projection data and that subsequently the sub-projection data are formed and the further reconstruction steps are executed.

3. A computed tomography method as claimed in claim 1, characterized in that first the sub-projection data are formed and that subsequently a pre-processing step for the reconstruction, notably weighting, logarithmation, filtering and/or rebinning of the projection data, as well as the further reconstruction steps are performed exclusively on the basis of the sub-projection data.

4. A computed tomography method as claimed in claim 1, further including a pre-processing step of local convolution for the sub-projection data.

5. A computed tomography method as claimed in claim 1, characterized in that the projection data are acquired as respective single projection data sets for each X-ray source position, and that a respective sub-projection data set is determined for each projection data set.

6. A computed tomography method as claimed in claim 1, characterized in that for the acquisition of the projection data the X-ray source and the X-ray detector rotate along a circular or helical trajectory around the object to be examined.

7. The method of claim 1 wherein the selected imaging zone includes an image slice which is inclined relative to the one or more images reconstructed from the projection data.

8. A computed tomography device for forming images of an object to be examined which is arranged in an examination zone, which device includes:
   an X-ray source for generating an X-ray beam which traverses the examination zone;
   means for rotating the X-ray source and an oppositely situated X-ray detector on the other side of the examination zone along a trajectory around the examination zone;
   an X-ray detector for the acquisition of projection data during the rotation;
   means for reconstructing one or more images from the projection data, wherein the one or more images reconstructed from the projection data include a first spatial orientation;
   means for using the one or more images to select an imaging zone of the object to be examined, wherein the selected imaging zone includes a second spatial orientation and the first and second spatial orientations are different;
   means for determining sub-regions of the X-ray detector on which the imaging zone of the object to be examined is projected during the acquisition of the projection data;
   means for forming sub-projection data by selecting the projection data associated with the sub-regions from the acquired projection data; and
   means for reconstructing a desired image of the selected imaging zone from the sub-projection data.

9. The device of claim 8 further including means for pre-processing the projection data on the basis of the complete, acquired projection data prior to the formation of the sub-projection data.

10. The device of claim 8 including means for pre-processing the sub-projection data, wherein the pre-processing is performed subsequent to the formation of and exclusively on the basis of the sub-projection data.

11. The device of claim 8 further including pre-processing means for performing a local convolution of the sub-projection data.

12. The device of claim 8 wherein the projection data are acquired as respective single projection data sets for each of a plurality of X-ray source positions, and wherein a respective sub-projection data set is determined for each projection data set.

13. The device of claim 8 wherein the trajectory is a circular or a helical trajectory and using the one or more images to select an imaging zone includes receiving a user input which identifies the desired imaging zone.

14. The device of claim 8 wherein the imaging zone is a curved surface, a line, or a curved plane.

15. The device of claim 8 wherein the imaging zone is inclined relative to the one or more images reconstructed from the projection data.

16. The device of claim 8 wherein the means for using selects an imaging zone having a spatial orientation which is substantially arbitrary relative to the first spatial orientation.

17. The device of claim 8 including a user input device which allows a user to select an imaging zone of substantially arbitrary orientation relative to the first spatial orientation.

18. A computed tomography method for forming images of an object to be examined which is arranged in an examination zone, which method includes the steps of:

generating, while using an X-ray source, a conical X-ray beam which traverses the examination zone of the object to be examined which is arranged therein;

rotating the X-ray source and an oppositely arranged X-ray detector on the other side of the examination zone along a trajectory around the examination zone;

acquiring projection data from the X-ray detector during the rotation;

reconstructing one or more images from the projection data;

using the one or more images to select an imaging zone of the object to be examined, wherein the selected imaging zone includes a line, a curved plane, or a curved surface;

determining sub-regions of the X-ray detector on which the imaging zone of the object to be examined is projected during the acquisition of the projection data;

forming sub-projection data by selecting the projection data associated with the sub-regions from the acquired projection data; and reconstructing one or more images of the selected imaging zone from the sub-projection data.

* * * * *